United States Patent [19]

Suyama

[11] Patent Number: 5,645,584
[45] Date of Patent: Jul. 8, 1997

[54] TYMPANOSTOMY TUBE AND METHOD FOR PRODUCING THE SAME

[75] Inventor: Takayuki Suyama, Chiba, Japan

[73] Assignee: Suyama Dental Laboratory Inc., Chiba, Japan

[21] Appl. No.: 604,607

[22] Filed: Feb. 21, 1996

[51] Int. Cl.$^6$ ........................................... A81F 2/18
[52] U.S. Cl. ........................ 623/10; 623/11; 623/12
[58] Field of Search ........................... 623/1, 10, 11, 623/12

[56] References Cited

U.S. PATENT DOCUMENTS

| | | | |
|---|---|---|---|
| 4,094,303 | 6/1978 | Johnston | 128/1 R |
| 4,650,488 | 3/1987 | Baus et al. | 623/12 |
| 4,744,792 | 5/1988 | Sander et al. | 623/10 |
| 5,047,053 | 9/1991 | Jahn | 623/10 |
| 5,171,270 | 12/1992 | Herrick | 623/11 |

OTHER PUBLICATIONS

*International Journal of Pediatric Otorhinolaryngology*, 16, S. D. Handler et al, pp. 55–60 (1988).

*Primary Examiner*—David Isabella
*Assistant Examiner*—John M. Black
*Attorney, Agent, or Firm*—Nikaido, Marmelstein, Murray & Oram LLP

[57] ABSTRACT

Disclosed are a tympanostomy tube made of pure titanium or a titanium alloy comprising a lumen formed longitudinally in an elongated tubular member and a concavity inwardly formed on said elongated tubular member in a circumferential direction at right angles to a longitudinal direction thereof, said lumen being longitudinally different in diameter and having a larger diameter at a position at which the concavity is not formed than at a position at which the concavity is formed; and a method for producing a tympanostomy tube comprising the steps of drilling a hole longitudinally in a rod member of pure titanium or a titanium alloy to form an elongated tubular member, and forming a concavity on said elongated tubular member in a circumferential direction at right angles to a longitudinal direction thereof.

1 Claim, 4 Drawing Sheets

TYMPANOSTOMY TUBE AND METHOD FOR PRODUCING THE SAME

FIELD OF THE INVENTION

The present invention relates to a tympanostomy tube and a method for producing the same, and more particularly to a tympanostomy tube used for drainage of fluids from the middle ear cavity and ventilation thereof in the treatment of otitis media, etc. and a method for producing the same.

BACKGROUND OF THE INVENTION

For the treatment of middle ear disorders such as exudative otitis media and blue drum (middle ear cholesterin granuloma), treatment instruments called "tympanostomy tubes" are inserted through the tympanic membrane by myringotomy, retained for an appropriate period of time to drain the exudates from the middle ear cavity to the outside through the tubes, and drawn out after the functional recovery of the middle ear.

The tympanostomy tubes therefore necessitate the easy insertion through an incision in the tympanic membrane, the efficient drainage of the exudates (viscous fluids), and no extrusion (no falling) from the tympanic membrane for a short period of time. Further, the tubes are required to be excellent in affinity for organisms, and to cause no allergy. The tubes also necessitate the easy infusion of steroid fluids and the easy removal of residual fluids when the steroid fluids are infused therethrough. Furthermore, it is also required that the inside of the middle ear cavity can be easily observed through the tubes in the treatment.

Various kinds of tubes have been proposed as the tympanostomy tubes. For example, a tube 4 shown in FIG. 1(A) is called a grommet type tube, and made of a polyethylene resin (coated with a silicone compound). This tube is expanded in the trumpet form by the viscous exudates as indicated by the arrows after its insertion. A tube 4 shown in FIG. 1(B) is formed of a Teflon resin as an integral body in the hourglass form. A tube 4 shown in FIG. 1(C) is similarly formed of a Teflon resin as an integral body in such a form that it can be easily retained in parallel with the external auditory meatus. A tube 4 shown in FIG. 1(D) is called a wide-collar type tube, and made of a silicone compound. An internal flange 8 is enlarged to enable long-term retention, and notches 9 are formed for easy insertion. A tube 4 shown in FIG. 1(E) is a T type tube, and made of a silicone compound. An inner flange 10 can be folded when inserted, and unfolded in the T form after insertion. A tube 4 shown in FIG. 1(F) is called a Castelli vent type tube, and made of a silicone compound. This tube is provided with internal and external flanges 11. A tube 4 shown in FIG. 1(G) is a parallel type tube, and made of a silicone compound. This tube has a structure similar to that of the tube 4 shown in FIG. 1(F). However, notches 12 are formed in the internal flange.

Further, tympanostomy tubes (permanent ventilation tubes of the middle ear) are also described in U.S. Pat. Nos. 3,982,545 and 5,047,053.

Furthermore, tympanostomy tubes made of titanium are described in S. D. Handler et al., *International Journal of Pediatric Otorhinolaryngology*, 16, 55–60 (1988).

Such a tympanostomy tube is inserted through the tympanic membrane, for example, as shown in FIGS. 2(A) and 2(B). The tympanic membrane 1 is incised, for example, laterally, as shown in FIG. 2(B), and a tube 4 is retained in the incision 2 thus formed by use of a tube insertion instrument 3 such as a forceps as shown in FIG. 2(A). In FIG. 2(A), reference numeral 5 designates the external ear cavity (external auditory meatus), reference numeral 6 designates the tympanic cavity, reference numeral 7 designates the middle ear cavity, and reference numeral 10 designates the exudate accumulated in the middle ear cavity.

Although various kinds of tympanostomy tubes are thus proposed, the grommet type tube shown in FIG. 1(A) has the advantage of easy insertion, but the disadvantage of easy extrusion. The tube 4 shown in FIG. 1(E) has the advantage of difficult extrusion due to the flange unfolded in the T form, but the disadvantage of inferior drainage caused by the T-shaped structure. The conventional tympanostomy tubes further include the following general common disadvantages.

That is, as shown in FIG. 1(H), any one of these tubes has a lumen 13 having the same diameter throughout the length thereof. FIG. 1(H) indicates a cross sectional view of the tube 4 shown in FIG. 1(B) as a typical example. As a result, these tubes have the disadvantage that the inside of the middle ear cavity is difficult to be observed after insertion thereof in the treatment.

In this case, the lumens 13 may be increased in diameter to make it easy to observe the inside of the middle ear cavity. However, these tubes are generally made of plastics or rubbers, so that an increase in diameter of the lumens 13 necessarily causes a thin wall thickness, resulting in decreased strength and easy deformation. The diameter of the lumens must therefore be necessarily decreased, which makes it difficult to observe the inside of the middle ear cavity. A smaller diameter is liable to result in inferior drainage of the exudates. A problem is therefore encountered in the infusion of steroid fluids and the removal of residual fluids when the steroid fluids are infused through the tubes.

Further, plastics and rubbers have the disadvantage of being poor in affinity for organisms. It is also considered that the tubes are formed of metals such as gold (Au) alloys. However, the gold alloys are heavy, having a high specific gravity, and have problems with regard to processability and cost.

The conventional tympanostomy tubes therefore have merits and demerits, and can not be fully satisfied.

SUMMARY OF THE INVENTION

It is therefore an object of the present invention to provide a tympanostomy tube through which the inside of the middle ear cavity is easily observed in the treatment, which is easily inserted through an incision in the tympanic membrane, through which the exudates (viscous fluids) are efficiently drained, resulting in excellent drainage, which are not extruded (do not fall) from the tympanic membrane for a short period of time, which are excellent in affinity for organisms and cause no allergy, and through which steroid fluids are easily infused and residual fluids are easily removed when the steroid fluids are infused therethrough.

The foregoing and other objects and novel features of the present invention will become clear from the following description and the accompanying drawings.

According to the present invention, there is provided a tympanostomy tube used in the treatment of a middle ear disorder such as otitis media, which is made of pure titanium or a titanium alloy, and comprises a lumen formed longitudinally in an elongated tubular member and a concavity inwardly formed on said elongated tubular member in a circumferential direction at right angles to a longitudinal direction thereof, said lumen being longitudinally different in diameter and having a larger diameter at a position at which the concavity is not formed than at a position at which the concavity is formed.

The present invention further provides a method for producing a tympanostomy tube comprising the steps of drilling a hole longitudinally in a rod member of pure titanium or a titanium alloy to form an elongated tubular member, and forming a concavity on said elongated tubular member in a circumferential direction at right angles to a longitudinal direction thereof.

BRIEF DESCRIPTION OF THE DRAWINGS

FIG. 3(A) is a perspective view for illustrating the step of drilling a hole, FIG. 3(B) is a perspective view showing the tube after drilling, and FIG. 3(C) is a perspective view for illustrating the step of forming a concavity.

DESCRIPTION OF THE PREFERRED EMBODIMENTS

The present invention will hereinafter be described with reference to the accompanying drawings.

Figure 1A:
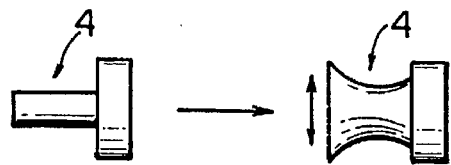
FIGS. 1(A) to 1(G) are schematic views showing examples of conventional tympanostomy tubes.
Figure 1B:
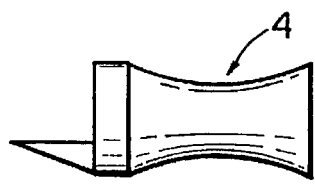
Figure 1C:
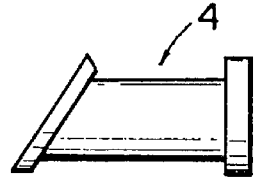
Figure 1D:
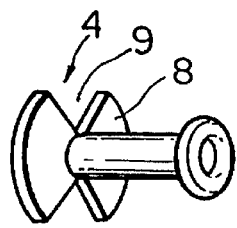
Figure 1E:
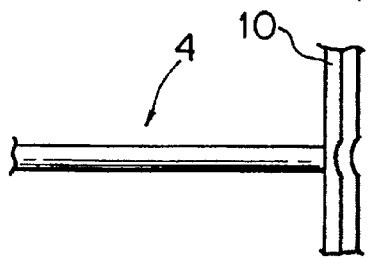
Figure 1F:
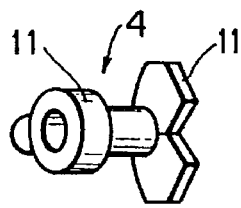
Figure 1G:
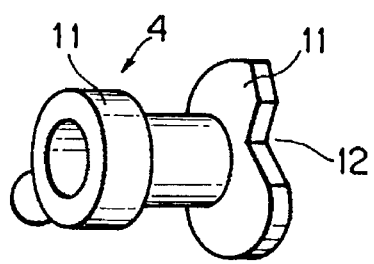
Figure 1H:
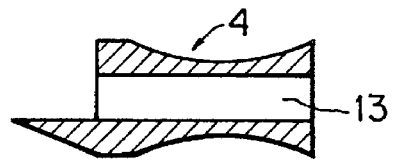
FIG. 1(H) is a cross sectional view of the tube shown in FIG. 1(B)
Figure 2A:
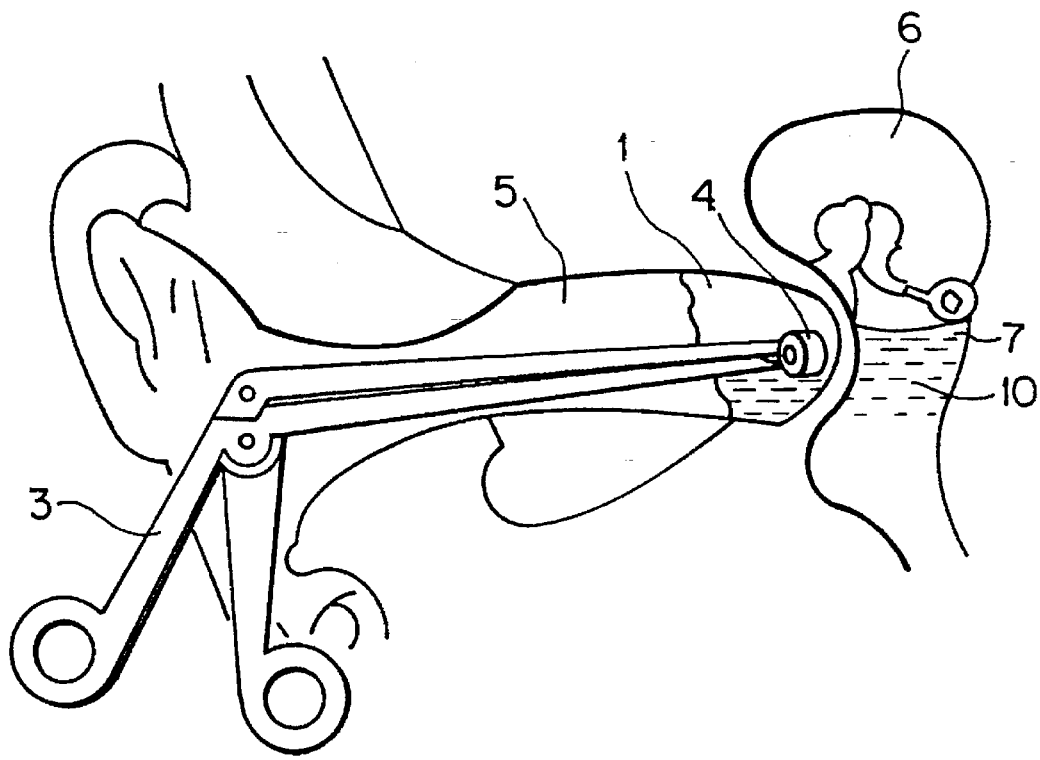
FIGS. 2(A) and 2(B) are views for illustrating insertion of a tympanostomy tube.
Figure 2B:
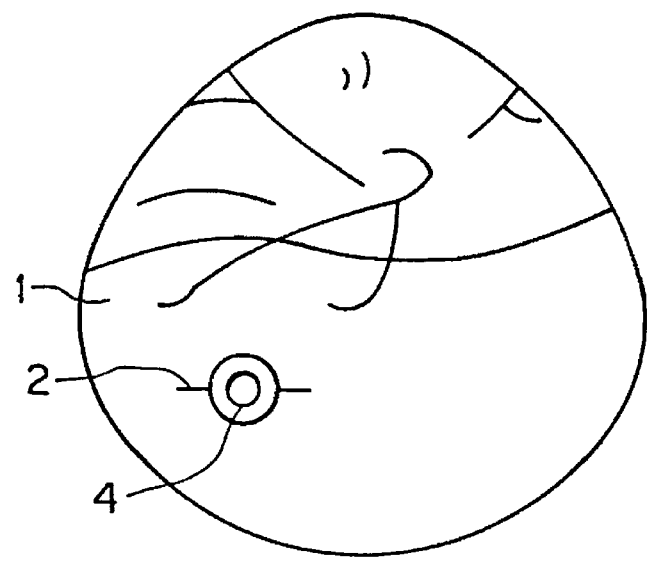
Figure 3A:
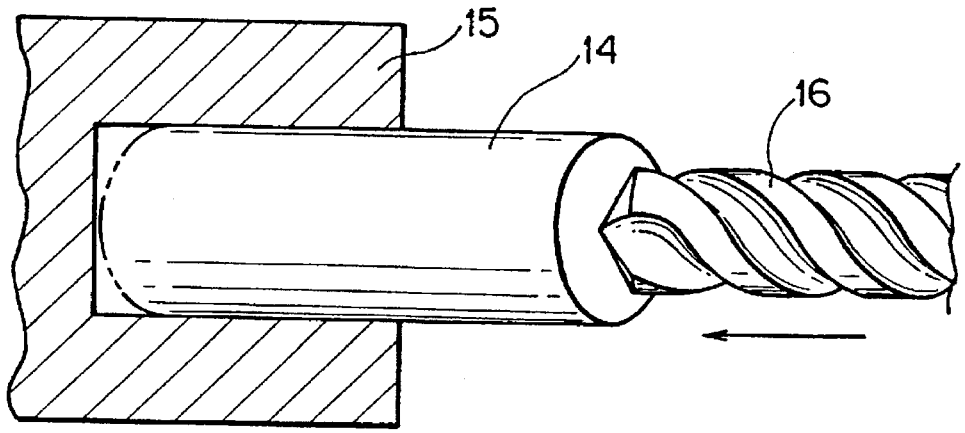
FIGS. 3(A) to 3(C) are perspective views for illustrating a method of producing a tympanostomy tube.
Figure 3B:
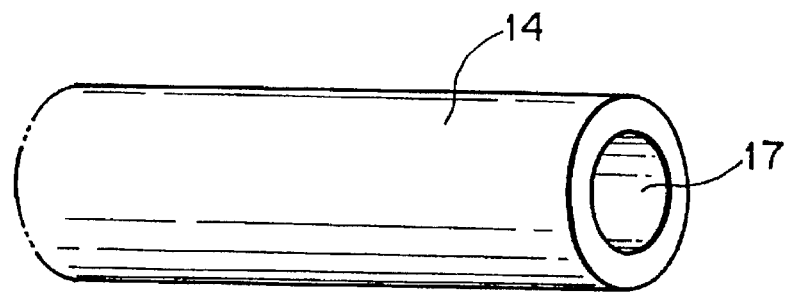
Figure 3C:
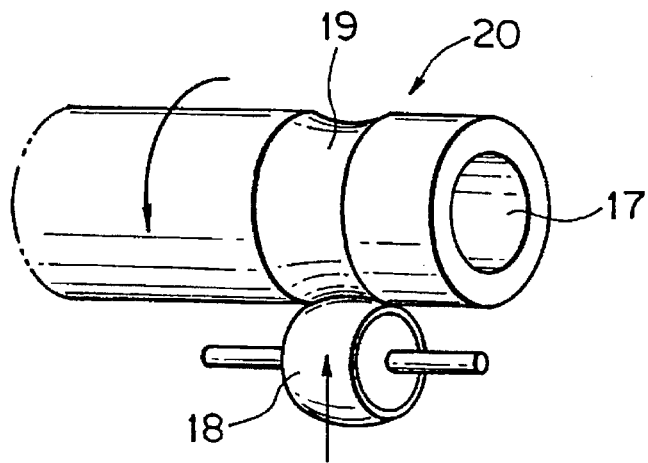

A method for producing a tympanostomy tube of the present invention is illustrated in FIGS. 3(A) to 3(C). As is shown in FIG. 3(A), a round rod 14 of pure titanium or a titanium alloy is held by a chuck 15 of a lathe.

As is shown in FIG. 3(A), rotation and axial linear feed are given to a drill 16 to drill a hole in the round rod 14 of pure titanium or a titanium alloy.

As is shown in FIG. 3(B), a lumen 17 is formed axially (in the longitudinal direction of the tube) in the round rod 14 of pure titanium or a titanium alloy by the drilling.

Then, a grinding wheel-like pressing jig 18 is pressed on the drilled round rod 14 of pure titanium or a titanium alloy (an elongated tubular member) at an intermediate position thereof in parallel with the axis of the round rod 14, while rotating the round rod 14, as is shown in FIG. 3(C).

As is shown in FIG. 3(C), the pressing forms a concavity 19 on the round rod 14 at the intermediate position in a circumferential direction at right angles to a longitudinal direction thereof.

Then, the round rod 14 is cut in an appropriate length, thereby obtaining a tympanostomy tube of the present invention.

Although not shown in the drawings, the present invention may further contain the steps of planing, shaping and milling a surface of the round rod 14 by use of a cutting tool and boring the lumen 17 already formed to widen it, thereby finishing it to a desired size and accuracy.

Figure 4:
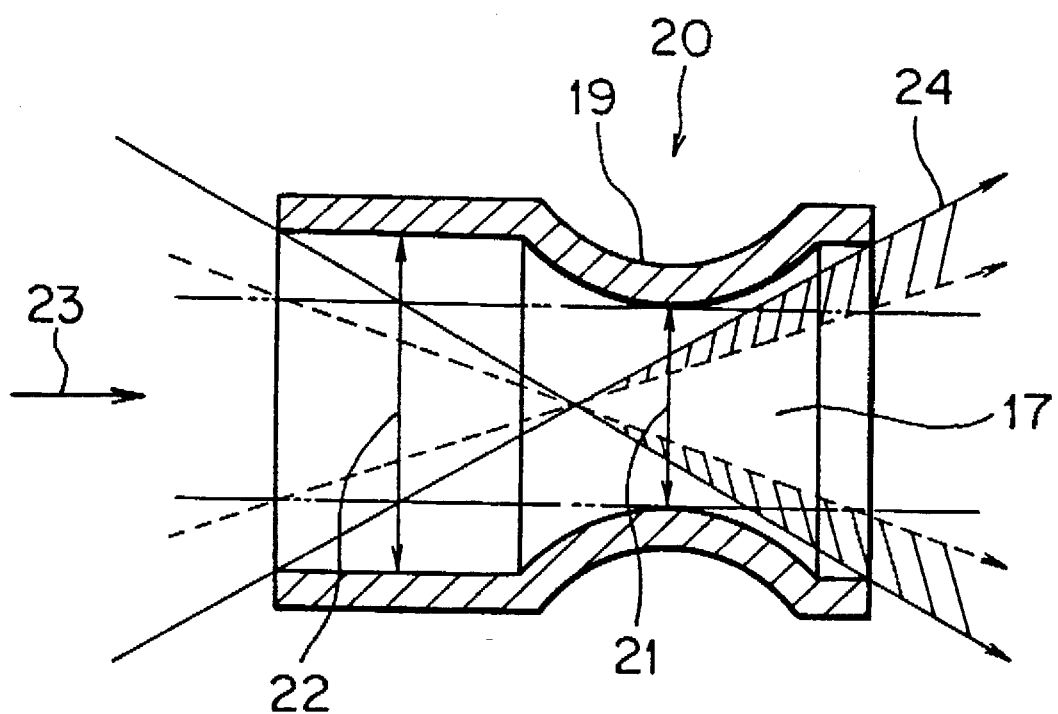
FIG. 4 is a cross sectional view showing a tympanostomy tube embodying the present invention.

FIG. 4 shows a cross sectional view of a tympanostomy tube embodying the present invention.

As is shown in FIG. 4, the tympanostomy tube 20 comprises a lumen 17 formed longitudinally in an elongated tubular member and a concavity 19 inwardly formed on said elongated tubular member in a circumferential direction at right angles to a longitudinal direction thereof. The lumen 17 is not uniform in diameter throughout the length thereof and longitudinally different in diameter. Namely, the diameter 21 of the lumen 17 at a position at which the concavity 19 is formed is different from the diameter 22 at the other positions (the diameter of the lumen before the formation of the concavity).

The diameter 22 is larger than the diameter 21.

Examples of pure titanium or the titanium alloys used for forming the round rods 14 in the present invention include titanium of class I, II or III standardized by the Japanese Industrial Standards (JIS). The composition of titanium of JIS class I is C % ($\leq 0.10$), H % ($\leq 0.013$), O % ($\leq 0.15$), N % ($\leq 0.05$), Fe ($\leq 0.20$) and Ti % (the balance). The composition of titanium of class II is the same as that of class I except for O % ($\leq 0.20$), and the composition of titanium of class III is the same as that of class I except for O % ($\leq 0.30$).

As is described above, if the round rod 14 can be held by the chuck 15 of the lathe and can be drilled with the drill 16, it is possible to form the large lumen in the round rod. The use of pure titanium or the titanium alloy as the constituent member of the tube improves the processability and increases the mechanical strength, which makes it possible to hold the round rod 14 with the chuck 15 of the lathe and to drill a hole in it with the drill 16. Even when a large hole is drilled in the longitudinal direction of the rod member, namely even when the wall thickness is decreased, deformation is hard to occur because of the high mechanical strength.

According to the tympanostomy tube of the present invention, therefore, the inside of the middle ear cavity is easily observed in the treatment, and the exudates (viscous fluids) are efficiently drained, resulting in excellent drainage.

Further, the pressing jig 18 can be pressed on the rod member to inwardly form the concavity 19 thereon in a circumferential direction at right angles to a longitudinal direction thereof, because of its good processability and high mechanical strength. Such formation of the concavity makes it possible to form flange portions at both ends of the tube. Pinching one flange of the tube with a forceps, etc., the tympanostomy tube can be easily inserted through an incision in the tympanic membrane. The tympanostomy tube has the flange portions at both ends, so that the viscous exudates are efficiently drained through the flange portions at both ends. Further, steroid fluids can be easily infused and residual fluids can be easily removed when the steroid fluids are infused through one flange portion of the tube.

On the other hand, when the conventional plastics (rubbers) are used as constituent members for tympanostomy tubes, it is difficult to apply such a method. It is further generally difficult to form the large lumens in the round rods, and it is also difficult to provide the concavities on the rod members in a circumferential direction at right angles to a longitudinal direction thereof to form the lumens different in diameter. When the diameter of the lumens is increased for the plastic (rubber) rod members, the wall thickness is necessarily decreased, which causes the low strength of the tubes, resulting in easy deformation. Accordingly, the diameter of the lumens must be necessarily decreased. As a result, it becomes difficult to observe the inside of the middle ear cavity in the treatment. A smaller diameter is liable to result in inferior drainage of the exudates. A problem is therefore encountered in the infusion of steroid fluids and the removal of residual fluids when the steroid fluids are infused through the tubes.

As is described above, the tympanostomy tube of the present invention structurally has the advantage that the inside of the middle ear cavity is easily observed in the treatment, because the concavity 19 is formed, the flange portions are formed at both ends of the tube, the lumen 17 is not uniform in diameter throughout the length thereof and longitudinally different in diameter, and the diameter 21 of the lumen 17 at a position at which the concavity 19 is formed is different from the diameter 22 at a position at which the concavity is not formed (the diameter of the lumen before the formation of the concavity). When the inside of the middle ear cavity is observed from the direction indicated by the arrow 23 shown in FIG. 4, the scope is indicated by the solid lines 24. The visual field is enlarged by shaded parts, compared with the scope indicated by the dotted lines.

Furthermore, the tympanostomy tube of the present invention has the flange portions at both ends of the tube, so that it is not extruded for a short period of time, making it possible to retain it for a long period of time.

Moreover, the tympanostomy tube of the present invention is made of pure titanium or the titanium alloy, so that it is low in specific gravity, excellent in strength, easily passivated, and good in biocompatibility to a degree similar to ceramics such as alumina. The tympanostomy tube therefore has also the advantage that the wall thickness can be decreased to form a lightweight tube. The tympanostomy tube can be obtained by drilling a hole in the round rod 14 to form the lumen 17, and pressing the pressing jig 18 thereon. Accordingly, the tympanostomy tube can be simply produced. In addition, the use of pure titanium or the titanium alloy can reduce costs.

Although the present invention has been described with reference to preferred embodiments, it is to be understood that the invention is not limited to the above-mentioned specific embodiments and that various changes and modifications may be made in the invention without departing from the spirit and scope thereof.

The effects obtained by the typical embodiments disclosed in the present invention are briefly described below.

Namely. according to the present invention, the tympanostomy tube can be obtained through which the inside of the middle ear cavity is easily observed in the treatment, which is easily inserted through an incision in the tympanic membrane, through which the exudates (viscous fluids) are efficiently drained, resulting in excellent drainage, which are not extruded (do not fall) from the tympanic membrane for a short period of time, which are excellent in affinity for organisms and cause no allergy, and through which steroid fluids are easily infused and residual fluids are easily removed when the steroid fluids are infused therethrough.

I claim:

1. A tympanostomy tube used in the treatment of a middle ear disorder, which is made of pure titanium or a titanium alloy, said tympanostomy tube comprising an elongated tubular member having a lumen formed longitudinally therein, said tubular member having substantially uniform diameter over the length thereof, said tubular member defining a wall of substantially uniform thickness, and said wall having a concavity inwardly formed on a portion of said elongated tubular member in a circumferential direction at right angles to a longitudinal direction thereof, said concavity being spaced from one end of said tubular member to form a flange portion on said tubular member, said lumen being longitudinally different in diameter and having a smaller diameter at a position at which the concavity is formed than at a position at which the concavity is not formed.

* * * * *